(12) United States Patent  
Sabb et al.

(10) Patent No.: US 6,239,134 B1  
(45) Date of Patent: May 29, 2001

(54) DIAZOLE DERIVATIVES AS SEROTONERGIC AGENTS

(75) Inventors: Annmarie L. Sabb, Pennington; Robert L. Vogel, Stratford, both of NJ (US); Michael G. Kelly, Newbury Park, CA (US); Yvette L. Palmer, Yardley; Wayne E. Childers, Levittown, both of PA (US)

(73) Assignee: American Home Products Corp., Madison, NJ (US)

( * ) Notice: Subject to any disclaimer, the term of this patent is extended or adjusted under 35 U.S.C. 154(b) by 0 days.

(21) Appl. No.: 09/515,049

(22) Filed: Feb. 25, 2000

Related U.S. Application Data

(60) Provisional application No. 60/155,230, filed on Mar. 3, 1999.

(51) Int. Cl.[7] .................... A61K 31/496; A61P 25/22; A61P 25/24; C07D 295/033
(52) U.S. Cl. .................... 514/253.1; 514/326; 544/367; 546/209
(58) Field of Search .................... 544/367; 514/253.1

(56) References Cited

U.S. PATENT DOCUMENTS

| | | | |
|---|---|---|---|
| 3,655,663 | 4/1972 | Wasson | 260/247.1 |
| 4,539,318 | 9/1985 | Baldwin et al. | 514/222 |
| 5,405,853 | 4/1995 | Baker et al. | 548/128 |
| 5,773,452 | 6/1998 | Sauerberg et al. | 546/268.7 |

FOREIGN PATENT DOCUMENTS

| | | |
|---|---|---|
| 0462638 | 12/1991 | (EP) . |
| 9427966 | 12/1994 | (WO) . |
| 9638431 | 5/1996 | (WO) . |
| 9638461 | 12/1996 | (WO) . |
| 9734899 | 9/1997 | (WO) . |

Primary Examiner—Richard L. Raymond  
Assistant Examiner—Venkataraman Balasubramanian  
(74) Attorney, Agent, or Firm—Joseph M. Mazzarese

(57) ABSTRACT

The present invention provides compounds of the general formula (1):

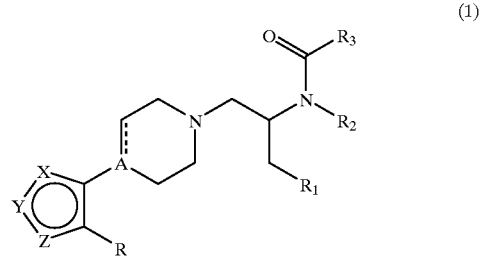

(1)

wherein:

two atoms of X, Y, or Z are nitrogen and the third atom is sulfur or oxygen;

R is H, halogen, OH, SH, $C_1$–$C_6$ alkyl, $C_1$–$C_6$ alkoxy, $C_1$–$C_6$ thioalkyl, phenoxy, thiophenoxy, phenyl or substituted phenyl;

A is C, CH, or N;

$R_1$ is aryl, heteroaryl, or cycloalkyl groups, optionally substituted by from 1 to 3 substituents selected from $C_1$–$C_6$ alkyl, $C_1$–$C_6$ alkoxy; $CF_3$, Cl, Br, F, CN, or $CO_2CH_3$;

$R_2$ is H or alkyl $R_3$ is $C_1$–$C_6$ alkyl, optionally substituted aryl, optionally substituted 5- or 6-membered heteroaryl, $C_3$ to $C_8$ cycloalkyl optionally substituted by $C_1$–$C_6$ alkyl, or a 3 to 8-membered heterocyclic ring containing one or more heteroatoms selected from O, S or N; or a pharmaceutically acceptable salt thereof, as well as pharmaceutical compositions and methods of treating central nervous system disorders using these compounds.

14 Claims, No Drawings

DIAZOLE DERIVATIVES AS SEROTONERGIC AGENTS

This application claims the benefit of U.S. Provisional Application No. 60/155,230, filed Mar. 3, 1999.

This invention relates to a series of novel diazolepiperazine, diazolepiperidine, and diazoledihydropiperidine derivatives, and to processes for their preparation, to pharmaceutical compositions containing them, and to their use in therapies concerning central nervous system disorders. These compounds are useful for treatment of conditions related to or affected by the 5-hydroxytryptamine-1-A (5-HT1A) receptor subtype in the CNS, including alcohol and drug withdrawl, sexual dysfunction, and Alzheimer's Disease. The utility of these compounds lies in their ability to bind as agonists and antagonists to 5-HT1A receptors. The compounds of the present invention are also useful in the treatment of depression and related CNS disorders (e.g., OCD, anxiety and panic) when combined with the use of serotonin reuptake inhibtors, such as Prozac® (fluoxetine hydrochloride).

BACKGROUND OF THE INVENTION

Depression is a psychiatric condition thought to be associated with decreased serotonin release. Most antidepressant agents potentiate the effects of serotonin by blocking the termination of its activity through re-uptake into nerve terminals.

U.S. Pat. No. 3,655,663 (B.K. Wasson, Apr. 11, 1972) covers 4-(3-secondary amino-2-hydroxypropoxy)-1,2,5-thiadiazoles which exhibit beta-adrenergic blocking properties useful for treatment of angina pectoris. Compounds of the present invention are structurally different from this prior art and are useful for treatment of CNS disorders.

WO 96/38431 (Eli Lilly, May 31, 1996) covers methods of making 1,2,5-thiadiazoles containing azacyclic or azabicyclic ether or thioether substituents for use as muscarinic cholinergic agonists. These compounds are useful as stimulants of the forebrain and hippocampus for treatment of Alzheimer's disease. Compounds of this invention are structurally different from these compounds and are agonists and antagonists of the 5HT1A receptor, not muscarinic agonists.

SUMMARY OF THE INVENTION

Compounds of the present invention are represented by the general formula (1):

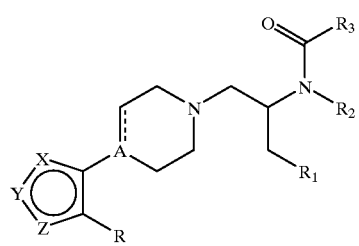

(1)

wherein:
two atoms of X, Y, or Z are nitrogen and the third atom is sulfur or oxygen;
R is H, halogen, OH, SH, $C_1$–$C_6$ alkyl, $C_1$–$C_6$ alkoxy, $C_1$–$C_6$ thioalkyl, phenoxy, thiophenoxy, or phenyl, the phenyl ring being optionally substituted by from one to three substituents selected from $C_1$–$C_6$ alkyl; $C_1$–$C_6$ alkoxy; $CF_3$; Cl; Br; F; CN; or $CO_2CH_3$;

A is C, CH, or N;
$R_1$ is aryl, heteroaryl, or cycloalkyl groups, the aryl, heteroaryl or cycloalkyl groups being optionally substituted by from 1 to 3 substituents selected from $C_1$–$C_6$ alkyl, $C_1$–$C_6$ alkoxy; $CF_3$, Cl, Br, F, CN, or $CO_2CH_3$;
$R_2$ is H or $C_1$–$C_6$ alkyl;
$R_3$ is $C_1$–$C_6$ alkyl, aryl, 5- or 6-membered heteroaryl, $C_3$ to $C_8$ cycloalkyl, the cycloalkyl groups being optionally substituted by $C_1$–$C_6$ alkyl, or a 3 to 8-membered heterocyclic ring containing one or more heteroatoms selected from O, S or N, the aryl and 5- or 6-membered heteroaryl groups being optionally substituted by from one to three substituents selected from $C_1$–$C_6$ alkyl, $C_1$–$C_6$ alkoxy, $CF_3$, Cl, Br, F, CN, or $CO_2CH_3$;
or a pharmaceutically acceptable salt thereof.

As used herein, the term alkyl refers to $C_1$–$C_6$ straight or branched chain, and wherein the term cycloalkyl refers to $C_3$ to $C_8$ ring, preferably a $C_3$ to $C_6$ ring, or an alkyl-substituted ring. The term "aryl" is phenyl or substituted phenyl, biphenyl, 1 or 2-naphthyl and "heteroaryl" refers to 5 or 6 membered ring heterocycles or benzofused heterocycles, specifically including, but not limited to, thiazole, thiophene, 2, 3, or 4-pyridyl, benzothiophene, or indole. The aryl or heteroaryl groups herein can be optionally substituted with one to three substituents selected from the group consisting of $C_1$–$C_6$ alkyl; $C_1$–$C_6$ alkoxy; $CF_3$; Cl; Br; F; CN; $CO_2CH_3$.

Among the preferred compounds of this invention are those of formula (2):

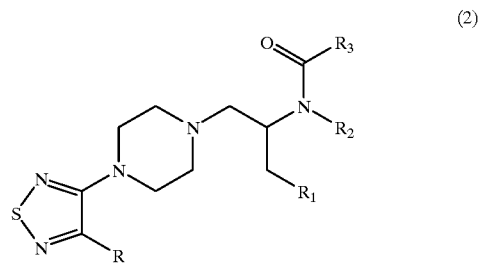

(2)

wherein R, $R_1$, $R_2$, and $R_3$, are as defined above, or a pharmaceutically acceptable salt thereof.

Further preferred are those compounds of formula (2) wherein:
R is H, halogen, OH, SH, $C_1$–$C_6$ alkyl, $C_1$–$C_6$ alkoxy, $C_1$–$C_6$ thioalkyl;
$R_1$ is aryl, heteroaryl, or cycloalkyl groups, optionally substituted by from 1 to 3 substituents selected from $C_1$–$C_6$ alkyl, $C_1$–$C_6$ alkoxy; $CF_3$, Cl, Br, F, CN, or $CO_2CH_3$;
$R_2$ is H or $C_1$–$C_6$ alkyl
$R_3$ is $C_1$–$C_6$ alkyl, optionally substituted aryl, optionally substituted 5- or 6-membered heteroaryl, $C_3$ to $C_8$ cycloalkyl optionally substituted by $C_1$–$C_6$ alkyl, or a 3 to 8-membered heterocyclic ring containing one or more heteroatoms selected from O, S or N;
or a pharmaceutically acceptable salt thereof.

The pharmaceutically acceptable salts are the acid addition salts which can be formed from a compound of the above general formula and a pharmaceutically acceptable acid such as phosphoric, sulfuric, hydrochloric, hydrobromic, citric, maleic, fumaric, acetic, lactic or methanesulfonic acid.

DETAILED DESCRIPTION OF THE INVENTION

The compounds of this invention possess high affinity for the serotonin 5-$HT_1$A receptor and, consequently, are useful as antidepressant and anxiolytic agents for the treatment in a mammal of a variety of central nervous system (CNS) disorders such as depression, anxiety, sleep disorders, sexual dysfunction, alcohol and/or cocaine addiction, and related problems. The compounds of this invention may also be used in the inducement of cognition enhancement in a mammal, preferably in humans. In addition, the compounds of this invention show marked selectivity for the 5-HT$_1$A receptors, as opposed to the α1 receptors.

In view of their receptor binding, these compounds may be characterized as anxiolytic and/or antidepressant agents useful in the treatment of depression and in alleviating anxiety. As such, the compounds may be administered neat o with a pharmaceutical carrier or excipient to a patient in need thereof. The pharmaceutical carrier may be solid or liquid.

It is understood that the therapeutically effective dosage to be used in the treatment of a specific psychosis must be subjectively determined by the attending physician. Variables involved include the specific psychosis or state of anxiety and the size, age and response pattern of the patient. The novel methods of the invention for treating, preventing or alleviating conditions as described above, or for inducing cognition enhancement, comprise administering to mammals in need thereof, including humans, an effective amount of one or more compounds of this invention or a non-toxic, pharmaceutically acceptable addition salt thereof. The compounds may be administered orally, rectally, parenterally, or topically to the skin and mucosa. The usual daily dose is depending on the specific compound, method of treatment and condition treated. An effective dose of 0.01–1000 mg/Kg may be used for oral application, preferably 0.5–500 mg/Kg, and an effective amount of 0.1–100 mg/Kg may be used for parenteral application, preferably 0.5–50 mg/Kg. It will be understood that in combination with other agonists or antagonists of the serotonin-1 receptor (5-HT$_1$A), such as those listed above, the effective dose of the present compounds may be reduced relative to the effective amount of the combined active ingredient(s).

The present invention also includes pharmaceutical compositions containing a compound of this invention, or a pharmaceutically acceptable salt thereof, and one or more pharmaceutically acceptable carriers or excipients. Applicable solid carriers or excipients can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical compositions and combination compositions of this invention are in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

Compounds of the present invention may be prepared by those skilled in the art of organic synthesis employing conventional methods which utilize readily available reagents and starting materials. The methods for preparing compounds of this invention will be further understood from the reaction schemes herein.

Referring to Scheme 1, the requisite dichlorodiazole is allowed to react with tert-butyl carboxy (BOC)-protected piperazine in an organic solvent, such as dimethylformamide (DMF) at elevated temperature under a nitrogen atmosphere to give the corresponding BOC-protected diazolepiperazines I. Treatment of the protected piperazines I with an acid such as hydrochloric acid, in an inert solvent, such as dioxane, under an inert atmosphere gives the deprotected piperazines II. Reaction of the diazolepiperazines II with nitrogen-protected amino acids, such as N-BOC-protected amino acids, in an organic solvent, such as methylene chloride, at room temperature under an inert atmosphere in the presence of an organic base, such as triethylamine (TEA), and a coupling reagent such as cyclohexylcarbodiimide (DCC) and hydroxybenzotriazole (HOBT) forms the amides III. Stirring the amides III with an acid, such as hydrochloric acid, in an organic solvent, such as dioxane, at room temperature under an inert atmosphere gives the amino amides IV. Reduction of the amides with diborane in an organic solvent, such as tetrahydrofuran (THF) gives the corresponding amines V. Acylation of the terminal amine with an acylating agent, such as an acyl halide or coupling of the amine with a carboxylic acid gives products of this invention VI.

Scheme 1

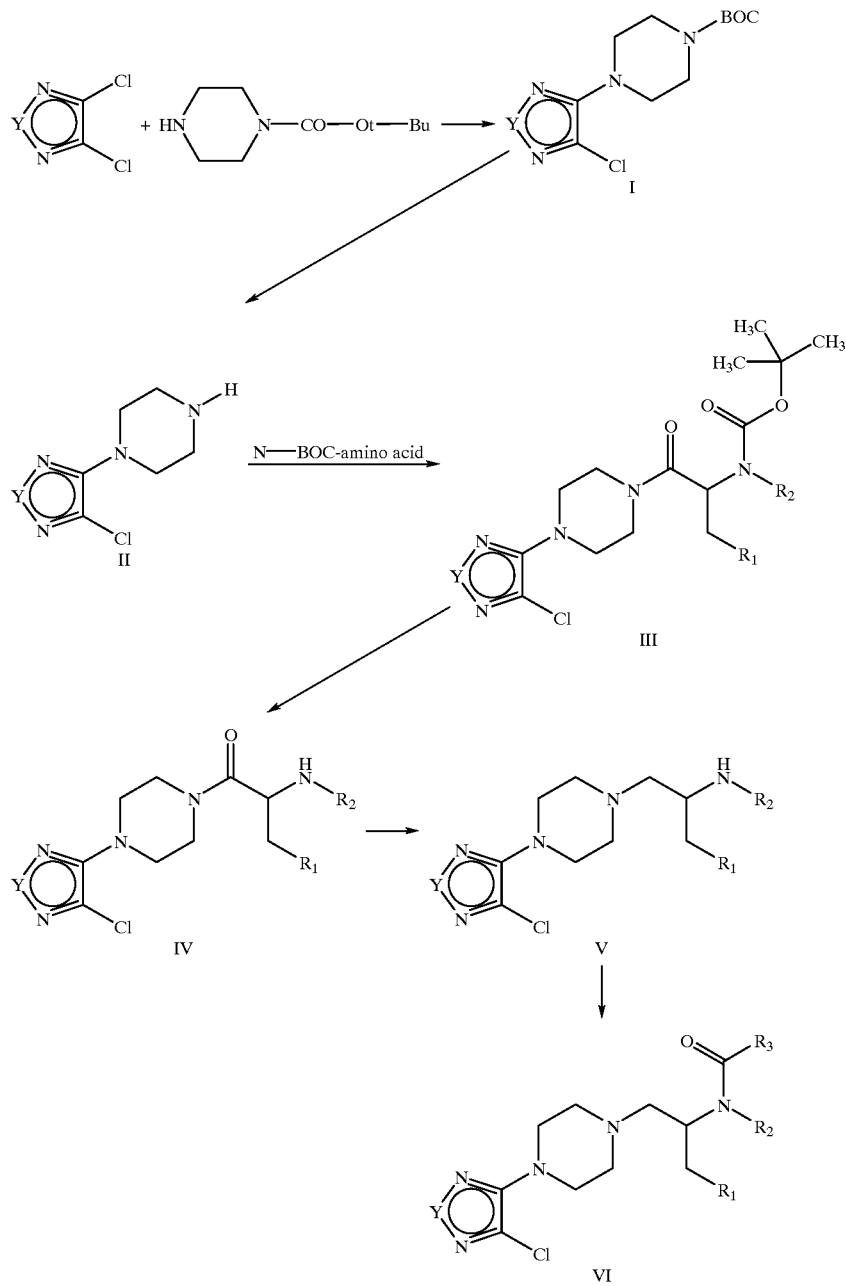

Referring to Scheme 2, the requisite chlorodiazolepiperazine II, is allowed to react with a metal, such as sodium, in a polar solvent, such as methanol, at elevated temperatures under an inert atmosphere to give diazolepiperazine derivatives VII. Allowing these piperazines VII to react with an N-BOC-protected amino acid and a coupling reagent, such as DCC in the presence of HOBT and a base, such as TEA, in an organic solvent, such as methylene chloride, gives the amides VIII. Stirring the amides VIII with an acid, such as hydrochloric acid, in an organic solvent, such as dioxane, gives the amino amides IX. Reduction of the amino amides IX with diborane in an organic solvent, such as THF, under an inert atmosphere, at elevated temperature gives the amines X. Acylation of the terminal amine with an acylating agent, such as an acyl halide, or coupling of the amines with a carboxylic acid gives products of this invention XI.

Scheme 2

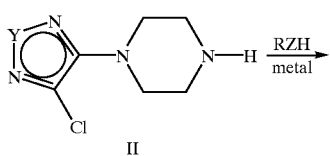

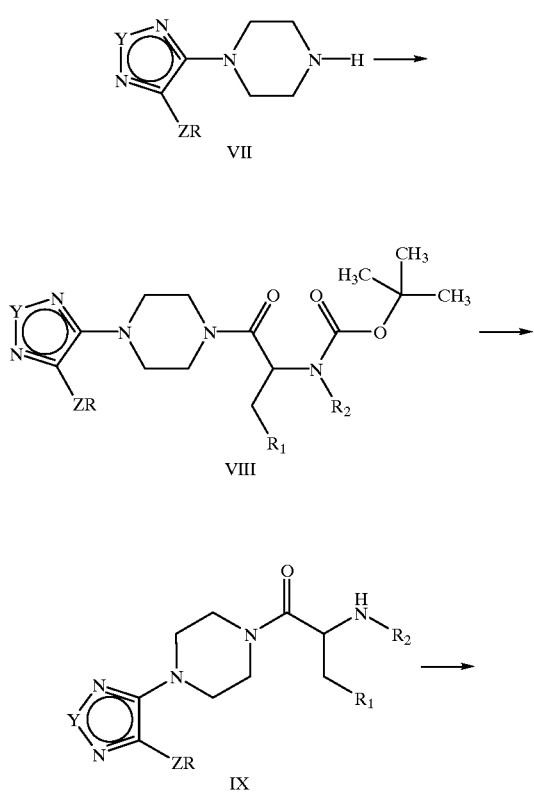

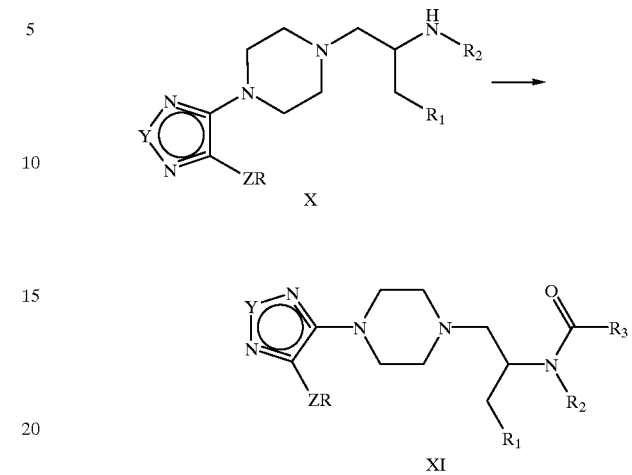

Referring to Scheme 3, the requisite chlorodiazolepiperazine amide III is allowed to react with a metal, such as sodium, in a polar solvent, such as methanol, at elevated temperatures under an inert atmosphere to give diazolepiperazine derivatives VIII. Stirring the amides VIII with an acid, such as hydrochloric acid, in an organic solvent, such as dioxane, gives the amino amides IX. Reduction of the amino amides IX with diborane in an organic solvent, such as THF, under an inert atmosphere, at elevated temperature gives the amines X. Acylation of the terminal amine with an acylating agent, such as an acyl halide, or coupling of the amines with a carboxylic acid gives products of this invention XI.

Scheme 3

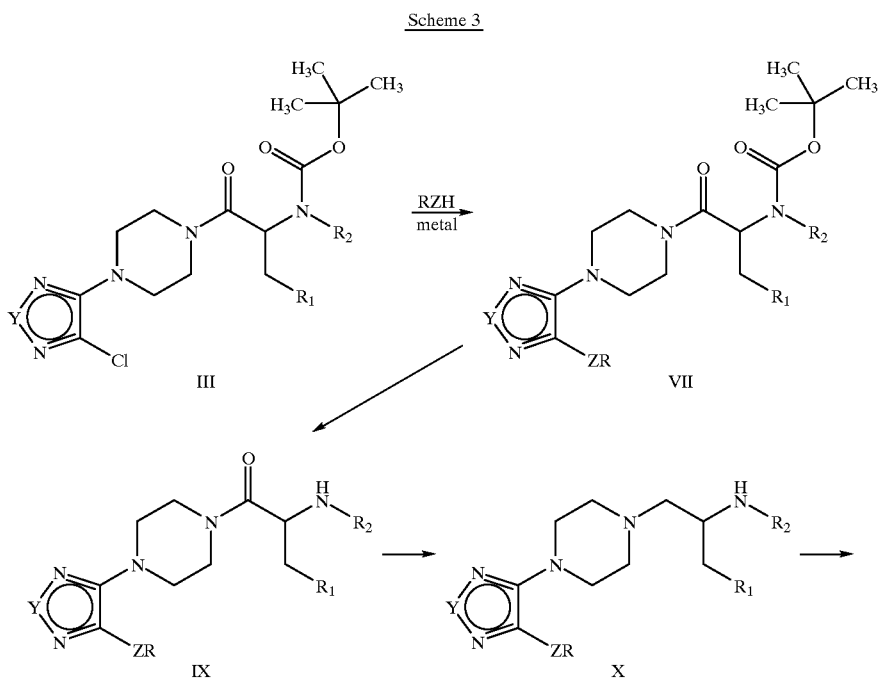

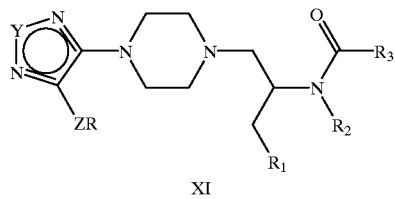

XI

Referring to Scheme 4, the N-protected 4-acylpiperidine or N-protected -4-acyldihydropiperidine is added to carbethoxyhydrazine in a polar solvent, such as methanol, at a low temperature, such as 0–5° C., and then heated under reflux to give the hydrazones XII. The hydrazones XII are heated from 30–100° C. in the presence of thionyl chloride to give 1,2,3-thiadiazole derivatives XIII. Deprotection of XIII gives the secondary amines XIV. Reaction of XIV with N-protected amino alcohols containing a leaving group, such as tosylate, in a polar solvent, such as dimethylsulfoxide, at elevated temperatures, such as 30–100° C., gives N-protected amine intermediates XV. Removal of the protecting group gives XVI and reaction of XVI with an acylating agent or with a carboxylic acid and a coupling reagent such as DCC gives compounds of this invention XVII.

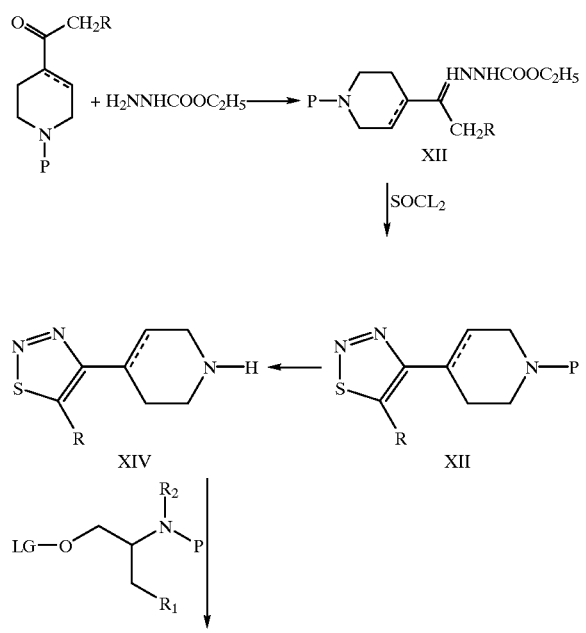

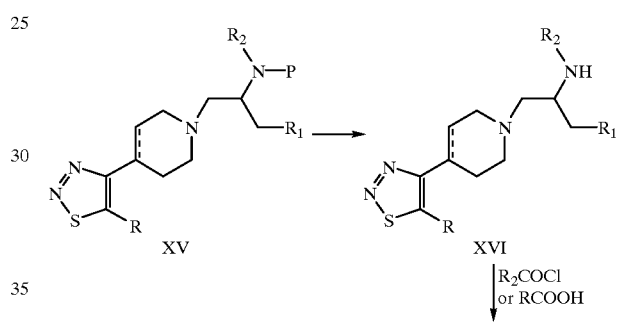

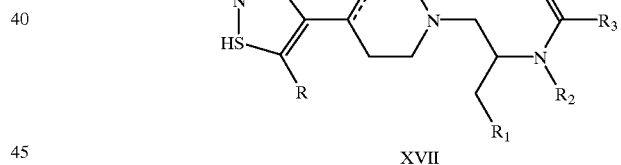

Referring to Scheme 5, 4-substituted pyridines XVIII which can be prepared by known methods [Per Sauerberg, et al. *J. Med. Chem.* 1992 35, 2274–2283] are protected on nitrogen by a group which can be removed, such as the N-carbethoxy group, to give XIX. XIX is reduced to XX using a reducing agent, such as $NaBH_4$. The protecting group is removed [for the BOC group an acid such as hydrogen chloride can be used] to give XXI which is allowed to react with an N-protected amino acid, such as a BOC-protected amino acid, to give amides XXII. Removal of the protecting group, such as treatment of the BOC group with an acid such as hydrogen chloride, gives XXIII. Reduction of the amides XXIII with a reducing agent such as diborane in an organic solvent such as tetrahydrofuran, gives XXIV. Acylation of XXIV with acylating agents or reaction of XXIV with carboxylic acids and a coupling agent such as DCC gives compounds of this invention XXV Scheme 5

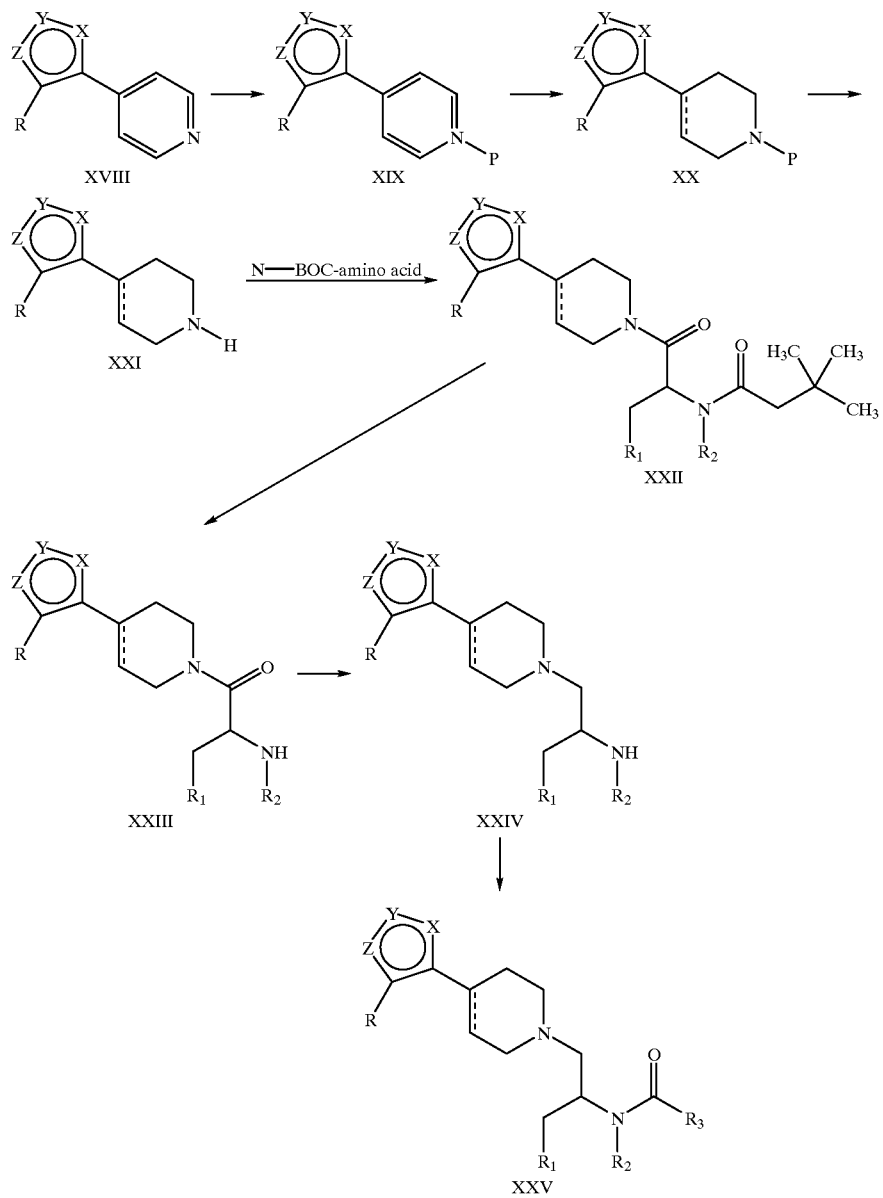

5-HT1A Receptor Binding Assay

High affinity for the serotonin 5-$HT_{1A}$ receptor was established by testing the claimed compound's ability to displace [3H] 8-OH-DPAT binding in CHO cells stably transfected with the human 5HT1A receptor. Stably transfected CHO cells are grown in DMEM containing 10% heat inactivated FBS and non-essential amino acids. Cells are scraped off the plate, transferred to centrifuge tubes, and washed twice by centrifugation (2000 rpm for 10 min., 4° C.) in buffer (50 mM Tris pH 7.5). The resulting pellets are aliquoted and placed at −80° C. On the day of assay, the cells are thawed on ice and resuspended in buffer. The binding assay is performed in a 96 well microtiter plate in a total volume of 250 mL. Non-specific binding is determined in the presence of 10 mM 5-HT, final ligand concentration is 1.5 nM. Following a 30 minute incubation at room temperature, the reaction is terminated by the addition of ice cold buffer and rapid filtration through a GF/B filter presoaked for 30 minutes in 0.5% PEI. Compounds are initially tested in a single point assay to determine percent inhibition at 1, 0.1, and 0.01 mM, and Ki values are determined for the active compounds.

5-HT1A Receptor Intrinsic Activity Assay

The intrinsic activity of compounds of the present invention was established by testing the claimed compounds ability to reverse the stimulation of cyclic adenosinemonophosphate (cAMP) in CHO cells stably transfected with the human 5-HT1A receptor.

Stably transfected CHO cells were grown in DMEM containing 10% heat inactivated FBS and non-essential amino acids. The cells are plated at a density of ×$10^6$ cells per well in a 24 well plate and incubated for 2 days in a $CO_2$ incubator. On the second day, the media is replaced with 0.5 mL treatment buffer (DMEM+25 mM HEPES, 5 mM theophylline, 10 mM pargyline) and incubated for 10 minutes at 37° C. Wells are treated with forskolin (1 mM final concentration) followed immediately by the test compound (0.1 and 1 mM for initial screen) and incubated for an additional 10 minutes at 37° C. The reaction is terminated by removal of the media and addition of 0.5 mL ice cold assay buffer (supplied in the RIA kit). Plates are stored at −20° C. prior to assessment of cAMP formation by RIA. $EC_{50}$ values are determined for the active test compounds. Compounds shown to have no agonist activities (Emax=0%) are further analyzed for their ability to reverse agonist induced activity. In separate experiments, 6 concentrations of antagonist are preincubated for 20 minutes prior to the addition of agonist and forskolin. Cells are harvested as described above. The cAMP kit is supplied by Amersham and the RIA is performed as per kit instructions, and calculations of $IC_{50}$ performed by GraphPad Prism.

| Compound | 5-HT1A binding Ki (nM) | cAMP Emax |
|---|---|---|
| Compound 4 | 0.84 | 93.00 ($EC_{50}$ = 4.61 nM) |
| Compound 5 | 425.20 | |
| Compound 6 | 47% @ 1 _M | |
| Compound 7 | 4.55 | 0.00 ($IC_{50}$ = 49.26 nM) |
| Compound 8 | 1.55 | 0.00 ($IC_{50}$ = 72.74 nM) |
| Compound 9 | 9.87 | |
| Compound 11 | 3.04 | 0.000 ($IC_{50}$ = 113.00 nM) |

The following non-limiting specific examples are included to illustrate the synthetic procedures used for preparing compounds of the formula 1. In these examples, all chemicals and intermediates are either commercially available or can be prepared by standard procedures found in the literature or are known to those skilled in the art of organic synthesis. Several preferred, non-limiting embodiments are described to illustrate the invention.

EXAMPLE 1

1-(4-Chloro-[1,2,5]thiadiazol-3-yl)piperazine Hydrochloride

Piperazine-1-carboxylic acid tert-butyl ester (10 g, 0.054 m) was dissolved in anhydrous dimethylformamide (DMF, 50 mL) under nitrogen in a single-necked round bottomed flask. The clear solution was placed in a preheated oil bath (50 C–60 C). 4,5-Dichloro-[1,2,5]thiadiazole (5.0 mL, 0.054 m) was added and the reaction mixture was allowed to stir for 24 h. A yellow solution containing a white solid was observed. After cooling to room temperature, the mixture was diluted with an equal volume of anhydrous ethyl ether and stirred for 5 minutes. The solid was removed by filtration and the yellow filtrate was concentrated under aspirator vacuum to remove ether and then evaporated under oil pump vacuum to remove DMF. The yellow residue was dried at oil pump vacuum overnight to give 9.91 g of 4-(4-chloro-[1,2,5]thiadiazol-3-yl)piperazine-1-carboxylic acid tert-butyl ester. Two recrystallizations of crude product from hexane gave white crystals: mp 83–86° C.
Anal. Calcd for $C_{11}H_{17}ClN_4O_2S \cdot 0.075$ mol hexane:
Theory: % C, 44.18;% H, 5.85;% N, 18.00
Found: % C, 44.44;% H, 5.84;%N, 17.80

The tert-butyl ester 1 (400 mg, 1.3 mmol) was treated with 4N HCl (5.0 mL) in dioxane under a nitrogen atmosphere. The ester dissolved and a white precipitate formed gradually. The mixture was allowed to stir overnight at room temperature. The reaction mixture was diltued with heptane and filtered to collect a crystalline solid which was rinsed with heptane and dried to give 285 mg of the title compound as a pale yellow solid, mp: 205° C. (dec).
Anal. Calcd. for $C_6H_9ClN_4S \cdot HCl \cdot 0.15\ H_2O$
Theory: % C, 29.56;% N, 4.26;% N, 22.98
Found: % C, 29.99;% N, 4.40;% N, 22.34

EXAMPLE 2

4-Piperazin-1-yl-[1,2,5]thiadiazole-3-ol Hydrochloride

The title compound of example 1 (1.25 g, 5.18 mmol), was combined with 2.5 N NaOH (10 mL) and dimethylsulfoxide (DMSO, 1.0 mL) and heated under reflux with stirring for 2.5 h. The heat was shut off and the cloudy mixture was allowed to cool and stir overnight. The pale yellow solution was chilled in an ice bath and acidified to pH 0 with concentrated HCl. The mixture was chilled in an ice bath for several hours and filtered to collect a white crystalline solid which was dried under reduced pressure over Drierite to give 0.469 g of the title compound, mp: 230° C. (dec).
Anal. Calcd. for $C_6H_{10}N_4S \cdot HCl \cdot 0.25\ H_2O$
Theory: % C, 31.69;% H, 5.06;% N, 24.65
Found: % C, 31.54;% H, 4.66;% N, 24.21

EXAMPLE 3

1-(4-Methoxy-[1,2,5]thiadiazol-3-yl)piperazine Hydrochloride

The title compound of Example 1 (0.95 g, 3.9 mmol) was suspended in anhydrous methanol (10 mL) under a nitrogen atmosphere. Pellets of sodium metal (0.733 g, 32 g-atoms) were added slowly with stirring. An exotherm to reflux occurred. Heating under reflux was continued for 2 h in preheated oil bath. The reaction mixture was then cooled to room temperature and allowed to stir overnight. The volatiles were removed under reduced pressure and the mustard-colored residue was partitioned between ethyl acetate and water. The aqueous phase was extracted with ethyl acetate (3x). The organic phases were combined, dried (MgSO4) and evaporated to give 0.268 g of a yellow oil. The oil was dissolved in methanol and treated with IM HCl in ether (2.0 mL) to give a tan solid which was recrystallized from 1:2 isopropanol:isopropyl ether to give 89 mg of the title compound as mustard yellow crystals, mp: 190° C. (dec).
Anal. Calcd. for $C_7H_{12}N_4OS \cdot HCl \cdot 0.1$ isopropanol
Theory: % C, 36.12;% H, 5.73;% N, 23.08.
Found: % C, 36.21;% H, 5.68;% N, 23.37.

EXAMPLE 4

Cyclohexanecarboxylic acid {(1S)-1-benzyl-2-(4-(4-chloro[1,2,5]thiadiazol-3-yl)piperazin-1-yl] ethyl}amide fumarate N-BOC-L-phenylalanine (6 g, 22.6 mmol) was dissolved in methylene chloride (240 mL) under a nitrogen atmosphere. To this was added the compound of Example 1 (5.0 g, 20.7 mmol) followed by triethylamine (TEA, 2.1 g), HOBT (3.65 g), and dicyclohexylcarbodiimide (DCC, 4.7 g). The reaction mixture was allowed to stir at room temperature overnight. The reaction mixture was filtered to remove insolubles and the volatiles was removed from the filtrate under reduced pressure. The residue was taken up in methylene chloride, cooled in a freezer, and filtered to remove a white solid. The filtrate was purified by chromatography on silica gel eluting with 0.4%–0.6% MeOH in methylene chloride to give Intermediate I ({1-benzyl-2-[4-(4-chloro[1,2,5]thiadiazol-3-yl)piperazin-1-yl]-2-oxo-ethyl}carbamic acid tert butyl ester) as an amorphous solid, mp: 45–51° C.

Anal. Calcd. for $C_{20}H_{26}ClN_5O_3S$
Theory: % C, 53.15;% H, 5.80;% N, 15.49
Found: % C, 53.02;% H, 5.64;% N, 15.27

Intermediate 1 (2.0 g) was dissolved in dioxane (5 mL) and treated with 4 M HCl in dioxane under a nitrogen atmosphere overnight. A mass of white solid was observed. The reaction mixture was diluted with dioxane and filtered to collect the solid. After drying under reduced pressure, 1.57 g of (2S)-2-amino-1-[4(4-chloro-[1,2,5]thiadiazol-3-yl)piperazin-1-]-3-phenylpropan-1-one hydrochloride [Intermediate II]: mp 201–205° C., was obtained.

Anal Calcd for $C_{15}H_{18}ClN_5OS$ . HCl.0.45 dioxane
Theory: % C, 47.15;% H, 5.32;% N, 16.36
Found: % C, 47.03;% H, 5.35;% N, 15.88

Intermediate 11 (0.92 g, 2.6 mmol) was dissolved in anhydrous THF (30 mL) under a nitrogen atmosphere. 1M $BH_3$ in THF (8.2 mL, 3 equivalents) was added (foaming) and the reaction mixture was heated under reflux 1 h. After cooling to room temperature, 1N HCl (10 mL) was added cautiously and stirring was continued overnight at room temperature. After extracting with ether, the aqueous phase was chilled in an ice bath and adjusted to pH 14 with solid NaOH. A yellow oil separated which was extracted into ethyl acetate, dried ($MgSO_4$), filtered, and evaporated to give a thick yellow oil which was dried under reduced pressure to give 376 mg of Intermediate III.

Intermediate III (357 mg, 1.06 mmol) was dissolved in anhydrous methylene chloride (20 mL) under a nitrogen atmosphere, followed by triethylamine (0.3 mL, 2 equivalents). Cyclohexylcarbonyl chloride (160 mg, 1 equivalent) was diluted with methylene chloride (10 mL) and added dropwise at 0–5 C. The reaction mixture was allowed to warm to room temperature and was stirred overnight. The reaction mixture was quenched with sat. $NaHCO_3$ (10 mL) and sat. NaCl (10 mL). The organic phase was separated, washed with water (2×), and dried ($MgSO_4$). The solution was filtered and the volatiles were removed under reduced pressure to give a viscous yellow oil was purified by flash column chromatography on silica gel eluting with up to 30% ethyl acetate in hexane to give 185 mg of the free base of the title compound. The compound was converted to the fumarate salt by treatment with fumaric acid in ethanol to give the title compound: mp, 138–140° C.

Anal Calcd for $C22H_{30}N_5ClOS.C_4H_4O_4$
Theory: %C, 55.36;%H, 6.08;%N, 12.41
Found: %C, 55.08;%H, 5.96;%N, 12.14

EXAMPLE 5

N-{(1S)-Benzyl-2-[4[(4-chloro-[1,2,5]thiadiazol-3-yl)piperazin-1-yl)ethyl)isonicotinamide Intermediate III (120 mg, 0.35 mmol) was dissolved in methylene chloride (15 mL) under nitrogen. Isonicotinic acid (50 mg, 0.41 mmol) was added followed by triethylamine (0.08 mL), 1-hydroxybenzotriazole hydrate, HOBT, (55 mg), and dicyclohexylcarbodiimide, DCC, (85 mg). The reaction mixture was stirred at room temperature overnight. After filtration to remove solids, volatiles were removed from the filtrate under reduced pressure. The residue was purified by flash column chromatography on silic gel eluting with methylene chloride to 2% methanol in methylene chloride to give the title compound, 100 mg, as a white solid.

The free base was converted to the fumarate salt using fumaric acid in ethanol and isopropyl ether. An amorphous solid was obtained. mp: 99–125° C.

Anal. Calcd. for $C_{21}H_{23}N_6ClOS.1.5\ C_4H_4O_4.0.75\ H_2O$
Theory: %C, 51.38;%H, 4.97;%N, 13.05.
Found: %C, 51.63;%H, 4.77;%N, 12.43

EXAMPLE 6

Pyridine-2-carboxylic acid {(1S)-1-benzyl-2,3-[4(4-chloro[1,2,5]thiadiazol-3-yl)piperazin-1-yl] ethyl}amide Example 6 was prepared using Intermediate III and pyridine-2-carboxylic acid according to the method of Example 5. The fumaric acid salt was a granular solid: mp 60–70° C.

Anal Calcd. For $C_21H_{23}N_6ClOS.C_4H_4O_4.\ 1\ H_2O.0.2$ diisopropylether
Theory: %C, 52.67;%H, 5.36;%N, 14.07.
Found: %C, 52.89;%H, 5.05;%N, 13.59

EXAMPLE 7

Cyclohexanecarboxylic acid {(2R)-1-benzyl-2-[4-(4-chloro[1,2,5]thiadiazol-3-ylpiperazin-1-1yl] ethyl}methylamide The compound of Example 1 and BOC-protected N-methyl-D-phenylalanine were allowed to react according to the method of Example 4 to give Intermediate IV, {(IR)-1-benzyl-2-[4-(4-chloro-[1,2,5]thiadiazol-3-yl)piperazin-1-yl]-2-oxo-ethyl}methylcarbamic acid tert-butyl ester: mp 109–111 C.

Intermediate IV was allowed to react with 4N HCl in dioxane according to the method of Example 4 to give Intermediate V, (2R)-1-[4-(4-chloro[1,2,5]thiadiazol-3-yl) piperazin-1-yl)-2-methylamino-3-phenylpropan-1-one: mp 230–232° C. chloride (0.08 mL) in methylene chloride (1 mL) at room temperature. After stirring for 5 minutes, 2.5 N NaOH (5 mL) and brine (12 mL) were added. The organic phase was separated and the aqueous was extracted with brine (2×). The combined organic phases were dried ($MgSO_4$), evaporated and the residue was purified on silica gel eluting with 1% methanol in methylene chloride to give 185 mg of the title compound as an oil. (89%). The free base was converted to the fumaric acid salt: mp 51–59° C.

Anal Calcd for $C_{23}H_{32}N_5OSCl+1.0\ C_4H_4O_4+1.0H_2O$
Theory: % C, 54.88;% H, 6.65;% N, 11.40.
Found: % C, 55.11;% H, 6.34;% N, 11.04.

EXAMPLE 8

Cyclohexanecarboxylic acid {(1R)-1-benzyl-2-[4-(4-methoxy-[1,2,5]thiadiazol-3-yl)-piperazine-1-yl] ethyl}methyl amide Intermediate IV of Example 7 (2.20 g. 4.9 mmole) was dissolved in warm methanol (50 mL) with stirring. Sodium spheres were added portionwise keeping the reaction mixture at reflux and following the reaction by mass spec. When the reaction was complete, the volatiles were removed under reduced pressure and the residue was partitioned between ethyl acetate and water. The aqueous phase was separated, extracted with ethyl acetate and the organic phases were combined, dried ($MgSO_4$), filtered, and evaporated to give an oily residue. The residue was purified by chromatography on silica gel eluting with 0.5% to 0.75% methanol in methylene chloride to give Intermediate VI as a tacky foam.

The foam was dissolved in anhydrous dioxane (20 mL), treated with 4 N HCl in dioxane (10 mL) and stirred at ambient temperature for 5 h. Ethyl ether (15 mL) was added and Intermediate VII was collected by filtration (800 mg, 40%) as a white solid, mp: 237–239 C (dec).

Intermediate VII (726 mg, 1.82 mmol) was reduced with IM $BH_3$ in THF (7 mL) containing TEA (0.3 mL) as described in Example 7. The crude product was purified by chromatography on silica gel eluting with 3.5% to 6% methanol in methylene chloride to give 398 mg (63%) of Intermediate VIII.

A solution of Intermediate VIII (298 mg, 0.86 mmol) in methylene chloride containing TEA (0.17 mL) was treated with a solution of cyclohexylcarbonyl chloride (0.17 mL) in methylene chloride (2 mL). After stirring for 15 minutes the reaction was quenched by the addition of brine (25 mL). The layers were separated and the aqueous phase was extracted twice with methylene chloride. The organic layers were combined, dried ($MgSO_4$), filtered, and evaporated to give a residue which was purified by chromatography on silica gel eluting with 0.5% methanol in methylene chloride to give the title compound (252 mg, 64%) as an oil. The oil was dissolved in ether, treated with ethereal HCl to give the HCl salt of the title compound as a white solid, mp: 190–193° C.
Anal. Calcd for $C_{24}H_{35}N_5O_2S+1.00$ HCl+0.4 $H_sO$
Theory: % C, 57.50;% H, 7.40;% N, 13.97.
Found: % C, 57.78;% H, 7.12;% N, 13.49.

EXAMPLE 9

N-{1-Benzyl-2-[4-(4-methoxy-[1,2,5]thiadiazol-3-yl)piperazin-1-yl]ethyl}-N-methylbenzamide A solution of Intermediate VIII (100 mg, 0.29 mmol) in methylene chloride containing TEA (0.12 mL) was treated with a solution of benzoyl chloride (0.05 mL) in methylene chloride (1 mL). After stirring for 4 hours the reaction was quenched by the addition of brine (10 mL). The layers were separated and the aqueous phase was extracted twice with methylene chloride. The organic layers were combined, dried ($MgSO_4$), filtered, and evaporated to give a residue which was purified by chromatography on silica gel eluting with 0.3–0.5% methanol in methylene chloride to give the title compound (90 mg, 69%) as an oil. The oil was dissolved in ether, treated with ethereal HCl to give the HCl salt of the title compound as a white solid, mp: 211–215° C.
Anal. Calcd. For $C_{24}H_{29}N_5O_2S+HCl$
Theory: %C, 59.06;%H, 6.2;%N, 14.35
Found: %C, 58.69;%H, 6.18;%N, 14.16

EXAMPLE 10

Morpholine-4-carboxylic acid {1-benzyl-2-[4-(4-methoxy[1,2,5]thiadiazol-3-yl)piperazin-1-yl]ethyl}methylamide A solution of Intermediate VIII (100 mg, 0.29 mmol) in methylene chloride containing TEA (0.12 mL) was treated with a solution of morpholine carbonyl chloride (0.05 mL) in methylene chloride (1 mL). After stirring for 4 hours the reaction was quenched by the addition of brine (10 mL). The layers were separated and the aqueous phase was extracted twice with methylene chloride. The organic layers were combined, dried ($MgSO_4$), filtered, and evaporated to give a residue which was purified by chromatography on silica gel eluting with 0.3–0.5% methanol in methylene chloride to give the title compound (100 mg, 75%) as a waxy solid. The solid was dissolved in ether, treated with ethereal HCl to give the 2 HCl salt of the title compound as a white amorphous solid, mp: 68–97° C.
Anal. Calcd for $C_{22}H_{32}N_6O_3S+2HCl$
Theory: %C, 49.53;%H, 6.42;% N, 15.75
Found: %C, 49.74;%H, 6.66;%N, 15.64

EXAMPLE 11

1-Methylcyclohexanecarboxylic acid {(1R)-2-[4-(4-methoxy-[1,2,5]thiadiazol-3-yl)-piperazin-1-yl]-1-pyridin-3-ylmethyl ethyl}amide The compound of Example 1 was allowed to react with BOC-D-3-pyridylalanine according to the method of Example 1 to give Intermediate X, {(2R)-2-[4(4-chloro-[1,2,5]thiadiazol-3-yl)piperazin-1-yl]-2-oxopyridin-3-ylmethylethyl]carbamic acid tert butyl ester as an amorphous solid.
Anal. Calcd for $C_{19}H_{25}ClN_6O_3S$
Theory: %C, 50.38;%H, 5.56;%N, 18.55
Found: %C, 51.25;%H, 5.65;%N, 18.18

The method of Example 4 was used to convert Intermediate X to Compound 11 with the exception that methylcyclohexylcarbonyl chloride was used in place of cyclohexanecarbonyl chloride.
Anal. Calcd for $C_{23}H_{34}N_6O_2S+2HCl+0.33$ $H_2O$
Theory: %C, 51.40;%H, 6.87;%N, 15.64
Found: %C 51.38;%H, 6.90;%N, 15.21.

What is claimed:

1. A compound of the formula (1):

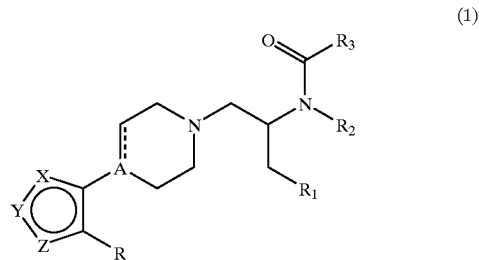

wherein:
two atoms of X, Y, or Z are nitrogen and the third atom is sulfur or oxygen;
R is H, halogen, OH, SH, $C_1$–$C_6$ alkyl, $C_1$–$C_6$ alkoxy, $C_1$–$C_6$ thioalkyl, phenoxy, thiophenoxy, or phenyl, the phenyl ring being optionally substituted by from one to three substituents selected from $C_1$–$C_6$ alkyl; $C_1$–$C_6$ alkoxy; $CF_3$; Cl; Br; F; CN; or;
A is N;
$R_1$ is aryl, thiazole, thiophene, 2-pyridyl, 3-pyridyl, 4-pyridyl, benothiophene, indole or cycloalkyl groups, the aryl, thiazole, thiophene, 2-pyridyl, 3-pyridyl, 4-pyridyl, benzothiophene, indole or cycloalkyl groups being optionally substituted by from 1 to 3 substituents selected from $C_1$–$C_6$ alkyl, $C_1$–$C_6$ alkoxy; $CF_3$, Cl, Br, F, CN, or $CO_2CH_3$;
$R_2$ is H or $C_1$–$C_6$ alkyl
$R_3$ is $C_1$–$C_6$ alkyl, aryl, thiazole, thiophene, 2-pyridyl, 3-pyridyl, 4-pyridyl, indole or $C_3$ to $C_8$ cycloalkyl optionally substituted by $C_1$–$C_6$ alkyl, the aryl, thiazole, thiophene, 2-pyridyl, 3-pyridyl, 4-pvridyl, or indole groups being optionally substituted by from one to three substituents selected from $C_1$–$C_6$ alkyl, $C_1$–$C_6$ alkoxy, $CF_3$, Cl, Br, F, CN, or $CO_2CH_3$;

or a pharmaceutically acceptable salt thereof.

2. A compound of claim 1 having the formula (2):

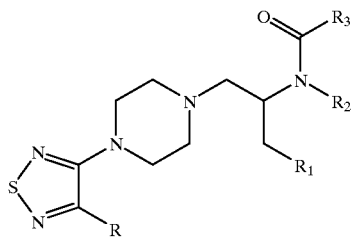

(2)

wherein R, $R_1$, $R_2$, and $R_3$, are as defined claim 1; or a pharmaceutically acceptable salt thereof.

3. A compound of claim 2 wherein:

R is selected from H, halogen, OH, SH, $C_1$–$C_6$ alkyl, $C_1$–$C_6$ alkoxy, or $C_1$–$C_6$ thioalkyl;

$R_1$ is selected from aryl, or cycloalkyl groups, optionally substituted by from 1 to 3 substituents selected from $C_1$–$C_6$ alkyl, $C_1$–$C_6$ alkoxy; $CF_3$, Cl, Br, F, CN, or $CO_2CH_3$;

$R_2$ is H or $C_1$–$C_6$ alkyl $R_3$ is $C_1$–$C_6$ alkyl, optionally substituted aryl, optionally substituted thiazole, thiophene, 2-pyridyl, 3-pyridyl, 4-pyridyl, or indole, or $C_3$ to $C_8$ cycloalkyl optionally substituted by $C_1$–$C_6$ alkyl; or a pharmaceutically acceptable salt thereof.

4. A compound of claim 1 which is Cyclohexanecarboxylic acid {(1S)-1-benzyl-2-[4-(4-chloro[1,2,5]thiadiazol-3-yl)piperazin-1-yl]ethyl}amide or a pharmaceutically acceptable salt thereof.

5. A compound of claim 1 which is N-{(1S)-1-Benzyl-2-[4-(4-chloro-[1,2,5]thiadiazol-3-yl)piperazin-1-yl]ethyl}isonicotinamide or a pharmaceutically acceptable salt thereof.

6. A compound of claim 1 which is Pyridine-2-carboxylic acid {(1S)-1-benzyl-2-[4-(4-chloro[1,2,5]thiadiazol-3-yl) piperazin-1-yl]ethyl}amide or a pharmaceutically acceptable salt thereof.

7. A compound of claim 1 which is Cyclohexanecarboxylic acid {2R)-1-benzyl-2-[4[(4-chloro[1,2,5]thiadiazol-3-yl) piperazin-1-yl]ethyl}methylamide or a pharmaceutically acceptable salt thereof.

8. A compound of claim 1 which is Cyclohexanecarboxylic acid {(IR)-1-benzyl-2-[4-(4-methoxy-[1,2,5]thiadizol-3-ylpiperazin-1-yl]ethyl}methylamide or a pharmaceutically acceptable salt thereof.

9. A compound of claim 1 which is N-{1-Benzyl-2-[4-(4-methoxy-[1,2,5]-thiadiazol-3-yl)piperazin-1-yl]ethyl}N-methylbenzamide or a pharmaceutically acceptable salt thereof.

10. A compound of claim 1 which is Morpholine-4-carboxylic acid {1-benzyl-2-[4-(4-methoxy-[1,2,5] thiadiazol-3-yl)piperazin-1-yl]ethyl}methylamide or a pharmaceutically acceptable salt thereof.

11. A compound of claim 1 which is 1-Methylcyclohexanecarboxylic acid {(1R)-2-[4-(4-methoxy-[1,2,5]thiadiazol-3-yl)-piperazin-1-yl]-1-pyridin-3-ylmethyl ethyl} amide or a pharmaceutically acceptable salt thereof.

12. A pharmaceutical composition comprising a pharmaceutically acceptable carrier or excipient and a compound of claim 1, or a pharmaceutically acceptable salt thereof.

13. A method for treating depression in a mammal, the method comprising administering to a mammal in need thereof a therapeutically effective amount of a compound of claim 1, or a pharmaceutically acceptable salt thereof.

14. A method for treating anxiety in a mammal, the method comprising administering to a mammal in need thereof a therapeutically effective amount of a compound of claim 1, or a pharmaceutically acceptable salt thereof.

* * * * *